United States Patent [19]

Stähle et al.

[11] 4,210,659
[45] Jul. 1, 1980

[54] SUBSTITUTED 7-PHENYL-2,3-DIHYDRO-IMIDAZO[1,2-α]IMIDAZOLES AND SALTS THEREOF

[75] Inventors: Helmut Stähle; Herbert Köppe; Werner Kummer, all of Ingelheim am Rhein, Fed. Rep. of Germany; Walter Kobinger, Vienna, Austria; Christian Lillie, Vienna, Austria; Ludwig Pichler, Vienna, Austria

[73] Assignee: Boehringer Ingelheim GmbH, Ingelheim am Rhein, Fed. Rep. of Germany

[21] Appl. No.: 52,566

[22] Filed: Jun. 27, 1979

[30] Foreign Application Priority Data

Jun. 23, 1978 [DE]  Fed. Rep. of Germany ....... 2827617

[51] Int. Cl.² .................. A61K 31/415; C07D 487/04
[52] U.S. Cl. ................................. 424/273 R; 548/324
[58] Field of Search ..................... 548/324; 424/273 R

[56] References Cited

U.S. PATENT DOCUMENTS 2,393,826  1/1946  Senkus ................................. 548/324
3,865,836  2/1975  Van Gelder et al. ................ 548/324

*Primary Examiner*—Natalie Trousof

*Attorney, Agent, or Firm*—Hammond & Littell, Weissenberger & Muserlian

[57] ABSTRACT

Compounds of the formula

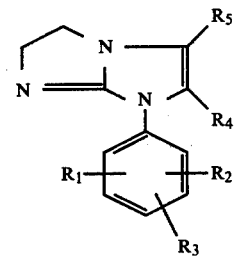

wherein
$R_1$, $R_2$ and $R_3$, which may be identical to or different from each other, are each hydrogen, fluorine, chlorine, bromine, methyl, methoxy or trifluoromethyl, provided that one of them is other than hydrogen; and
$R_4$ and $R_5$, which may be identical to or different from each other, are each hydrogen or methyl;
and non-toxic, pharmacologically acceptable acid addition salts thereof. The compounds as well as their salts are useful as bradycardiacs.

4 Claims, No Drawings

SUBSTITUTED 7-PHENYL-2,3-DIHYDRO-IMIDAZO[1,2-α]IMIDAZOLES AND SALTS THEREOF

This invention relates to novel derivatives of 7-phenyl-2,3-dihydro-imidazo[1,2-α]imidazole and acid addition salts thereof, to pharmaceutical compositions containing them as active ingredients, and to methods of using them as bradycardiacs.

More particularly, the present invention relates to a novel class of compounds represented by the formula

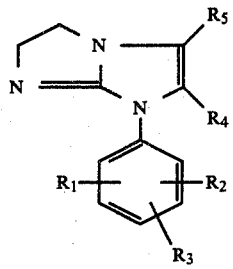

wherein
$R_1$, $R_2$ and $R_3$, which may be identical to or different from each other, are each hydrogen, fluorine, chlorine, bromine, methyl, methoxy, or trifluoromethyl, provided that one of them is other than hydrogen; and
$R_4$ and $R_5$, which may be identical to or different from each other, are each hydrogen or methyl;
and non-toxic, pharmacologically acceptable acid addition salts thereof.

The compounds embraced by formula I may be prepared by various methods involving known principles of chemical synthesis, among which the following have proved to be particularly convenient and efficient.

Method A

By reacting a phenylimino-imidazolidine of the formula

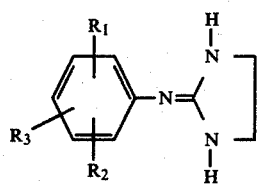

wherein $R_1$, $R_2$ and $R_3$ have the same meanings as in formula I, with a compound of the formula

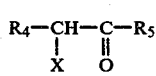

wherein
$R_4$ and $R_5$ have the same meanings as in formula I, and
X is chlorine, bromine or iodine.

The reaction is advantageously carried out by heating the reactants, preferably in the presence of a polar or nonpolar organic solvent, to a temperature between about 60°–180° C. The particular reaction conditions depend to a large extent upon the reactivity of the reactants. If desired or necessary, the reaction may be performed in the presence of an acid-binding agent such as triethylamine.

Method B

By cyclizing a 2-(N-propargyl-N-phenyl-amino)-2-imidazoline of the formula

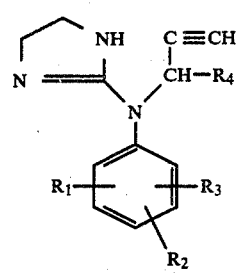

wherein $R_1$, $R_2$, $R_3$ and $R_4$ have the same meanings as in formula I, which yields the correspondingly substituted compound of the formula I wherein $R_5$ is methyl.

The cyclization is effected by heating the starting compound to an elevated temperature, preferable to between 50° and 150° C., in the presence of a polar or non-polar solvent and advantageously in the presence of an organic base such as trimethylbenzyl ammonium hydroxide.

Method C

By dehydrating a 7-phenyl-5-hydroxy-2,3,5,6-tetrahydroimidazo[1,2-α]imidazole of the formula

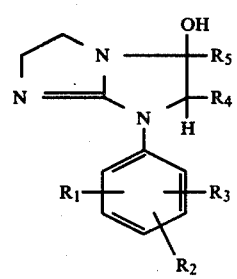

wherein $R_1$, $R_2$, $R_3$, $R_4$ and $R_5$ have the same meanings as in formula I, at a temperature between 60° and 180° C. or in the presence of a dehydrating agent. The reaction may be performed in the presence or absence of a solvent.

Method D

By reacting a 1-phenyl-2-imino-4-imidazoline of the formula

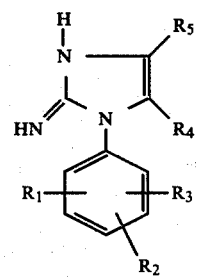

wherein $R_1$, $R_2$, $R_3$, $R_4$ and $R_5$ have the same meanings as in formula I, with 1,2-dibromo-ethane. The reaction is performed at elevated temperatures, preferably between 80° and 180° C., and may be carried out in the presence of a solvent, although the presence of a solvent is not required.

The starting compounds of the formula II are disclosed in Belgian Pat. Nos. 623,305, 687,657 and 705,944.

The compounds of the formula III are available in commerce and are described in the literature.

The starting compounds of the formula IV are disclosed in German Offenlegungsschrift No. 2,523,103.

The starting compounds of the formula V may be obtained by reacting a phenylimino-imidazolidine of the formula II with a compound of the formula III at low temperatures.

Finally, the starting compounds of the formula VI may be obtained by reacting a guanidine of the formula

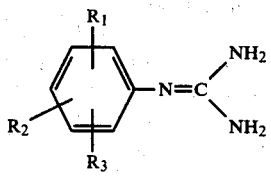

wherein $R_1$, $R_2$ and $R_3$ have the same meanings as in formula I, with a compound of the formula III.

The end products of the formula I are organic bases and therefore form acid addition salts with inorganic or organic acids. Examples of non-toxic, pharmacologically acceptable acid addition salts are those formed with mineral acids such as hydrochloric acid, hydrobromic acid, hydriodic acid, hydrofluoric acid, sulfuric acid, phosphoric acid or nitric acid, or organic acids such as acetic acid, propionic acid, butyric acid, caproic acid, caprinic acid, valeric acid, oxalic acid, malonic acid, succinic acid, maleic acid, fumaric acid, lactic acid, tartaric acid, citric acid, malic acid, benzoic acid, p-hydroxy-benzoic acid, p-amino-benzoic acid, phthalic acid, cinnamic acid, salicylic acid, ascorbic acid, methanesulfonic acid, ethanephosphoric acid, 8-chloro-theophylline or the like.

The following examples illustrate the present invention and will enable others skilled in the art to understand it more completely. It should be understood, however, that the invention is not limited solely to the particular examples given below.

EXAMPLE 1

7-(2,6-Dibromo-phenyl)-2,3-dihydro-5-methyl-imidazo[1,2-α]imidazole by method A

A mixture consisting of 9.6 gm (0.03 mol) of 2-(2,6-dibromophenyl-imino)-imidazoline, 2.6 ml (110% of the stoichiometrically required amount) of chloroacetone, 3 ml of triethylamine and 30 ml of absolute toluene was heated in a closed tube at 150° C. for 17 hours. Thereafter, the toluene phase was decanted, and the residue was dissolved in dilute hydrochloric acid. The resulting solution was fractionally extracted with ether at stepwisely increasing pH values (addition of 2 N sodium hydroxide). The thin-layer chromatographically pure ethereal fractions were combined, dried over anhydrous calcium sulfate and evaporated in vacuo, leaving 1.65 gm (15.4% of theory) of the compound of the formula

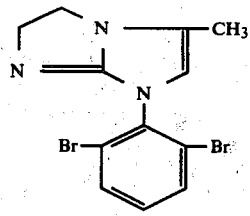

which had a melting point of 144°–147° C.

EXAMPLE 2

7-(2,6-Dichloro-phenyl)-2,3-dihydro-5-methyl-imidazo[1,2-α]imidazole by method B A mixture consisting of 5.4 gm of 2-[N-(2,6-dichloro-phenyl)-N-propargyl-amino]-2-imidazoline and 40 ml of ethanol containing 5 drops of trimethylbenzyl ammonium hydroxide was refluxed for five hours, while stirring. Thereafter, the ethanol was evaporated in vacuo, and the residue was dissolved in dilute hydrochloric acid. The resulting solution was fractionally extracted with ether at stepwisely increasing pH-values (addition of 2 N sodium hydroxide). The thin-layer chromatographically uniform ethereal fractions having a pH of 9 or more were combined, dried over magnesium sulfate, and the ether was evaporated in vacuo, leaving 1 gm (18.7% of theory) of 7-(2,6-dichloro-phenyl)-2,3-dihydro-5-methyl-imidazo[1,2-α]imidazole, m.p. 113°–117° C.

EXAMPLE 3

7-(2-Chloro-6-methyl-phenyl)-2,3-dihydro-imidazo[1,2-α]imidazole by method C 5 gm (0.02 mol) of 7-(2-chloro-6-methyl-phenyl)-5-hydroxy-2,3,5,6-tetrahydro-imidazo[1,2-α]-imidazole were slowly heated to 180° C. on an oil bath, while stirring, and allowed to remain at that temperature for about 5 minutes. The molten mass was allowed to cool, was then dissolved in dilute hydrochloric acid, and the solution was extracted once with ether. The ethereal extract solution was discarded. The acidic aqueous phase was made alkaline with 2 N sodium hydroxide and was then extracted several times with ether while salting out (common salt). The combined ethereal extracts were dried over anhydrous calcium sulfate and evaporated in vacuo, leaving 2.9 gm (63% of theory) of slightly impure reaction product, as determined by thin-layer chromatography. For further purification the product was twice stirred with ether and suction-filtered off, yielding 1.1 gm (23.9% of theory) of 7-(2-chloro-6-methyl-phenyl)-2,3-dihydro-imidazo[1,2-α]-imidazole, m.p. 105°–107° C.

EXAMPLE 4

7-(2,6-Dichloro-phenyl)-2,3-dihydro-imidazo-[1,2-α]imidazole by method D

A mixture consisting of 4.56 gm (0.02 mol) of 1-(2,6-dichloro-phenyl)-2-imino-4-imidazoline and 2.6 ml of ethylene bromide (about 150% of the stoichiometrically required amount) was heated to 140° C. while stirring and was maintained at that temperature for 15 minutes. After cooling, the glassy mass was dissolved in about 1

N hydrochloric acid, and the solution was friactionally extracted with ether at stepwisely increasing pH-values (addition of 2 N sodium hydroxide). Those fractions which contained the reaction product in substantially pure form, as determined by thin-layer chromatography, were combined, dried over anhydrous calcium sulfate and evaporated in vacuo. The residue was further purified by stirring it with acetone and collecting the crystallized product by suction filtration. 0.55 gm (10.8% of theory) of pure 7-(2,6-dichloro-phenyl)-2,3-dihydro-imidazo[1,2-a]imidazole, m.p. 184°–187° C. were obtained.

Using procedures analogous to those described in the preceding examples, the following compounds of the formula

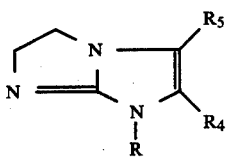

were also prepared. The melting points are those of the free bases unless otherwise indicated.

| Ex. No. | R | R⁴ | R⁵ | M.p. (°C.) | Yield (% of theory) |
|---|---|---|---|---|---|
| 5 | 2,4-Cl,Cl-C₆H₃ | H | CH₃ | 129–130 | 15.2 |
| 6 | 4-Cl, 2-CH₃-C₆H₃ | H | CH₃ | oil | 24.0 |
| 7 | 2-Cl, 5-CH₃-C₆H₃ | H | CH₃ | hydrobromide 260 | 6.6 |
| 8 | 2-Cl, 5-F-C₆H₃ | H | CH₃ | 113–116 | 17.2 |
| 9 | 2-CF₃-C₆H₄ | H | CH₃ | oil | 16.2 |
| 10 | 2,6-Cl,Cl-C₆H₃ | H | CH₃ | 128–130 | 14.9 |
| 11 | 2-CH₃, 6-Cl-C₆H₃ | H | CH₃ | 82–84 | 21.5 |
| 12 | 2,4-Br, 6-Br, F-C₆H₂ | H | CH₃ | 79–84 | 6.2 |
| 13 | 2-F, 6-CF₃-C₆H₃ | H | CH₃ | 86–91 | 19.8 |
| 14 | 2-Br, 5-F-C₆H₃ | H | CH₃ | 60–65 | 20.3 |
| 15 | 2-Cl, 5-F-C₆H₃ | H | CH₃ | 67–72 | 28.5 |
| 16 | 2,5-Br,Br-C₆H₃ | H | H | 155–158 | 10.9 |
| 17 | 2-F, 5-CF₃-C₆H₃ | H | H | 133.5–134.5 | 51.7 |
| 18 | 2-Cl, 5-CH₃-C₆H₃ | H | CH₃ | 99–103 | 25.6 |
| 19 | 2-Cl, 6-F-C₆H₃ | H | H | 129–133 | 42.1 |
| 20 | 2-Br, 6-F-C₆H₃ | H | H | 126–127 | 46.7 |
| 21 | 2-Br, 6-Cl-C₆H₃ | H | CH₃ | 139–141 | 30.7 |
| 22 | 2,6-Cl,Cl-C₆H₃ | CH₃ | CH₃ | 151–154 | 14.8 |
| 23 | 2,6-Br,Br-C₆H₃ | CH₃ | CH₃ | 149–152 | 8.5 |
| 24 | 2-Br, 6-F-C₆H₃ | CH₃ | CH₃ | 143–145 | 22.0 |
| 25 | 2-F, 6-CF₃-C₆H₃ | CH₃ | CH₃ | 142–143 | 15.1 |
| 26 | 2-Cl, 6-CH₃-C₆H₃ | CH₃ | CH₃ | oil | 7.6 |

-continued

| Ex. No. | R | $R^4$ | $R^5$ | M.p. (°C.) | Yield (% of theory) |
|---|---|---|---|---|---|
| 27 |  Cl, Br | H | $CH_3$ | 141–143 | 43.8 |

The compounds of the present invention, that is, those embraced by formula I above and their non-toxic, pharmacologically acceptable acid addition salts, have useful pharmacodynamic properties. More particularly, they exhibit bradycardiac activity in warm-blooded animals such as rats, and are therefore useful for the treatment of coronary diseases.

The bradycardiac properties of the compounds were ascertained on spinal rats. For instance, we have found that a dose of 0.42 mgm/kg of the compound of Example 1 above lowers the heart rate of spinal rats by 150 beats per minute.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective oral dosage unit of the compounds according to the present invention is from 0.0016 to 1.67 mgm/kg body weight, preferably 0.0083 to 0.83 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 28

Coated pills

The pill core composition is compounded from the following ingredients:

| | | |
|---|---|---|
| 7-(2,6-Dibromo-phenyl)-2,3-dihydro-5-methyl-imadazo-[1,2-α]imidazole | 5 parts | |
| Lactose | 65 parts | |
| Corn Starch | 130 parts | |
| Sec. calcium phosphate | 40 parts | |
| Soluble starch | 3 parts | |
| Magnesium stearate | 3 parts | |
| Colloidal silicic acid | 4 parts | |
| Total | 250 parts | |

Preparation

The active ingredient is admixed with a portion of all of the excipients, the mixture is thoroughly kneaded with an aqueous solution of the soluble starch, and the moist mass is granulated through a screen. The granulate is dried and intimately admixed with the remainder of the excipients, and the mixture is compressed into 250 mgm-pill cores which are then coated with a thin shell consisting essentially of a mixture of sugar, talcum and gum arabic. Each coated pill is an oral dosage unit composition containing 5 mgm of the active ingredient.

EXAMPLE 29

Hypodermic Solution

The solution is compounded from the following ingredients:

| | | |
|---|---|---|
| 7-(2,6-Dibromo-phenyl)-2,3-dihydro-5-methyl-imidazo-[1,2-α]imidazole | | 1.0 parts |
| Sodium chloride | | 18.0 parts |
| Distilled water | q.s.ad | 2000.0 parts by vol. |

Preparation

The active ingredient and the sodium chloride are dissolved in the distilled water, the solution is filtered until free from suspended particles, and the filtrate is filled into 2 cc-ampules which are subsequently sterilized and sealed. The contents of each ampule are an injectable dosage unit composition containing 1 mgm of the active ingredient.

EXAMPLE 30

Drop Solution

The solution is compounded from the following ingredients:

| | |
|---|---|
| 7-(2,6-Dichloro-phenyl)-2,3-dihydro-5-methyl-imidazo-[1,2-α]imidazole | 0.02 parts |
| Methyl p-hydroxy-benzoate | 0.07 parts |
| Propyl p-hydroxy-benzoate | 0.03 parts. |
| Demineralized water q.s. ad | 100.0 parts by vol. |

Preparation

The active ingredient and the p-hydroxy-benzoates are dissolved in a sufficient amount of demineralized water, the solution is diluted to the indicated volume with additional demineralized water and then filtered, and the filtrate is filled into 100 cc-bottles equipped with a dropping spout. 10 ml of the contents of the bottom are an oral dosage unit composition containing 2 mgm of the active ingredient.

Any one of the other compounds embraced by formula I or a non-toxic, pharmacologically acceptable acid addition salt thereof may be substituted for the particular active ingredient in Examples 28 through 30. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

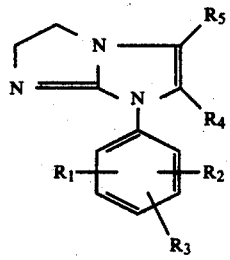

wherein

R₁, R₂ and R₃, which may be identical to or different from each other, are each hydrogen, fluorine, chlorine, bromine, methyl, methoxy or trifluoromethyl, provided that one of them is other than hydrogen; and R₄ and R₅, which may be identical to or different from each other, are each hydrogen or methyl;

or a non-toxic, pharmacologically acceptable acid addition salt thereof.

2. A compound of claim 1, which is 7-(2,6-dibromophenyl)-2,3-dihydro-5-methyl-imidazo[1,2-a]imidazole or a non-toxic, pharmacologically acceptable acid addition salt thereof.

3. A bradycardiac pharmaceutical dosage unit composition consisting essentially of an inert pharmaceutical carrier and an effective bradycardiac amount of a compound of claim 1.

4. The method of reducing the heart rate of a warm-blooded animal in need thereof, which comprises perorally or parenterally administering to said animal an effective bradycardiac amount of a compound of claim 1.

* * * * *